US005538890A

United States Patent [19]

Sands et al.

[11] Patent Number: 5,538,890

[45] Date of Patent: Jul. 23, 1996

[54] SELF-DELIMITING FUNGAL MUTANTS, BIOHERBICIDAL COMPOSITIONS THEREOF, METHOD OF PREPARING THEREOF AND METHOD OF USING THEREOF FOR WEED CONTROL

[75] Inventors: David C. Sands; Roger V. Miller, both of Bozeman, Mont.; Eugene Ford, Tok, Ak.; Gregory Kennett, Huson, Mont.

[73] Assignee: Research and Development Institute, Inc. at Montana State University, Boseman, Mont.

[21] Appl. No.: 928,488

[22] Filed: Aug. 13, 1992

Related U.S. Application Data

[63] Continuation-in-part of Ser. No. 283,822, Dec. 13, 1988, abandoned, which is a continuation-in-part of Ser. No. 79,963, Jul. 31, 1984.

[51] Int. Cl.$^6$ .............................. C12N 1/14; C12N 3/00

[52] U.S. Cl. .................. 435/254.1; 435/171; 435/172.1; 435/242; 435/260; 435/267; 435/911; 435/254.11; 47/DIG. 10; 935/64; 504/117

[58] Field of Search ............................ 435/34, 254, 911, 435/242, 260, 267, 171, 172.1; 424/93 R; 47/DIG. 10; 71/11, 69

[56] References Cited

U.S. PATENT DOCUMENTS

| | | | |
|---|---|---|---|
| 3,457,063 | 7/1969 | Neighbors | 504/322 |
| 3,503,732 | 3/1970 | Cahoy | 504/344 |
| 3,849,104 | 11/1974 | Daniel | 504/117 |
| 3,999,973 | 12/1976 | Templeton | 504/117 |
| 4,489,161 | 12/1984 | Papavizas | 424/93 |

OTHER PUBLICATIONS

Sands et al. Proc. 3rd. Intl Conf on Plant Pathogenic Bacteria, Geesteramis, H. P., Ed. Centre Agricultural Publications Documents, Wageningen, The Netherlands (1971).

Charu dattan, R. "The Use of Natural and Genetically Altered Strains of Pathogens for Weed Control" pp. 347–372 Biol. Control in Agric. IPM Systems, Acad. Press NY (1985).

*Primary Examiner*—Michael G. Wityshyn
*Assistant Examiner*—Jane Williams
*Attorney, Agent, or Firm*—Lowe, Price, LeBlanc & Becker

[57] ABSTRACT

A broad spectrum biological herbicide comprises a mammal-sparing bioherbicide fungal mutant, e.g., a *S. sclerotiorum* mutant, of limited survival time and geographical dissemination characteristics under standard agricultural conditions. The invention also relates to a method of obtaining herbicides of the invention comprising obtaining viable wild type bioherbicide fungal spores, subjecting these to UV light to reduce the number of viable fungi to less than 5% the initial number of spores, selecting mutants which differ from the wild type in at least one characteristic such as altered phenotype or morphology, and further selecting a mammal-sparing bioherbicide fungal mutant of reduced survival time and geographical dissemination characteristics under agricultural conditions when compared with the wild type. The invention also relates to a method of using the broad spectrum biological herbicide to reduce the number of weeds in an area. The invention also relates to a limited plant spectrum mammal-sparing bioherbicide. The invention further relates to a method for obtaining the bioherbicides according to the invention.

20 Claims, 9 Drawing Sheets

TOMato, DANdelion, BEAN, spotted KNAP-weed, SUNflower, ALFalfa
Disease: 0 no disease, 4 dead CONtrol, DICHONdra, PLANtain, white CLOVER, mock STRAWberry, BUTTONweed, DANDelion; 10 Days CONtrol, DICHONdra, PLANtain, DANDElion, BUTTONweed, mock STRAWberry, white CLOVER; 10 days CONtrol, PLANtain, DANDElion, DICHONdra
mock STRAWberry, BUTTONweed, white
CLOVER; 21 Days

SELF-DELIMITING FUNGAL MUTANTS, BIOHERBICIDAL COMPOSITIONS THEREOF, METHOD OF PREPARING THEREOF AND METHOD OF USING THEREOF FOR WEED CONTROL

This is a Continuation-in-Part of U.S. application Ser. No. 07/283,822, filed Dec. 13, 1988 now abandoned, which is a Continuation-in-Part of U.S. application Ser. No. 079, 963, filed Jul. 31, 1987, now abandoned, entitled "Self-delimiting Mutants of Plant Pathogens for Biological Control".

BACKGROUND OF THE INVENTION

1. Field of the Invention

This invention relates to mutants of plant pathogenic fungi, methods for their preparation, bioherbicidal compositions thereof and methods of using the mutants for weed control. The fungal mutants of the invention are agriculturally and environmentally acceptable and safe due to their inability to survive over prolonged periods of time.

2. Description of the Background

A variety of non-selective broad spectrum chemical herbicides are known and are utilized in situations requiring the control of various species of weeds growing simultaneously in a field (e.g., U. S. Pat. No. 3,503,732). Selective chemical herbicides are also known and are utilized when the eradication of a limited number of weeds is desired (e.g., U. S. Pat. No. 3,457,063).

In areas where chemical herbicides cannot be safely or economically utilized, the biological control of weeds is an alternative possibility. Approaches which have been used in the past for developing biological weed control agents have been of two different types.

The first relies on the isolation of native or exotic pathogens or pests which are highly effective and at the same time specific to a particular weed. This need for both specificity and effectiveness has severely limited the number of organisms that can be successfully used to control weeds (e.g., U.S. Pat. Nos. 3,999,973 and 3,849,104).

An alternative approach is the use of mutation and selection to isolate highly lethal but non-specific pathogens or pests which are limited to the area of application or to a target species (e.g., U.S. Pat. No. 4,489,161). In the '161 patent, disease causing organisms are mutated to obtain variant strains useful to reduce the deleterious effect of the plant pathogenic microorganism fusarium wilt on chrysanthemums. Sands, D. C., and Rovira, A. D., "Modifying the Virulence and Host Range of Weed Pathogens, p. 305, Proceedings Third Int. Conf. on Plant Pathogenic Bacteria, Geesteramis, H. P., Ed., Centre Agricultural Publications Documents, Wageningen, The Netherlands (by one of the present inventors) disclosed the preparation of a mutant Pseudomonas bacterium which is harmless to the single type of desired plants (tomato plants) but kills weeds such as nightshade. Charudattan, R., "The Use of Natural and Genetically Altered Strains of Pathogens for Weed Control", pp. 347–372, Biological Control in Agricultural IPM Systems, Academic Press, Inc., N.Y., (1985), discussed generally the use of genetically altered organisms for biological control of weeds.

Accordingly, the provision of a plant-sparing fungal bioherbicide useful for the control of weeds which does not persist in the environment for a prolonged period of time would be a great advance in the area of weed control.

STATEMENT OF DEPOSIT

Several subspecies of *S. sclerotiorum, including strains SL*-7 (ATCC Accession No. 74246), A6-Arg (ATCC Accession No. 74248), Al-Pyr (ATCC Accession No. 20929), and SL-1 (ATCC Accession No. (20930) as well as subspecies of Sclerotiumrolfsii, SrA6-Pyr (ATCC Accession No. 74247), and SrA4-Thi (ATCC Accession No. 74249) have been deposited with the American Type Culture Collection under the terms and conditions of the Budapest Treaty. The American Type Culture Collection is located at 12301 Parklawn Drive, Rockville, Md., 20852 USA. Two thousand series Accession No. deposits were made Mar. 24, 1989 and seven thousand series Accession No. deposits were made Sep. 28, 1993.

SUMMARY OF THE INVENTION

This invention relates to a broad spectrum bioherbicide comprising a mammal-sparing bioherbicide fungal mutant having substantially limited survival time and geographical dissemination characteristics under standard agricultural conditions.

The invention also relates to a broad spectrum mammal-sparing biocidal composition comprising a herbicidal amount of an inoculum of the bioherbicide described above, and an agriculturally-acceptable carrier.

This invention also relates to a method of obtaining the broad spectrum mammal-sparing bioherbicide described above, comprising

- obtaining viable wild type bioherbicide fungal spores;
- subjecting said spores to mutagenisis under conditions effective to reduce the number of viable fungi to less than about 5% of the initial number of spores;
- selecting fungal mutants which differ from said wild type fungus in at least one characteristic selected from the group consisting of altered phenotype and morphology; and
- further selecting a mammal-sparing herbicidal fungal mutant having substantially reduced survival time and geographical dissemination characteristics under standard agricultural conditions when compared with said wild type.

Also part of this invention is a method of reducing the number of weeds in an area while sparing mammals comprising applying to said weeds or said area a weed biocidal amount of an inoculum of a mammal-sparing bioherbicidal fungal mutant having substantially reduced survival time and geographical dissemination characteristics under standard agricultural conditions.

Also provided herein is a limited plant spectrum mammal-sparing weed biocidal composition comprising a weed biocidal amount of an inoculum of a mammal-sparing bioherbicide fungal mutant having substantially reduced plant spectrum biocidal activity when compared with the wild type, and an agriculturally acceptable carrier.

A more complete appreciation of the invention and many of the attendant advantages thereof will be readily perceived as the same becomes better understood by reference to the following detailed description of the preferred embodiments of the invention.

BRIEF DESCRIPTION OF THE DRAWINGS

Reference is now made to drawings wherein.

DESCRIPTION OF THE PREFERRED EMBODIMENTS

Figure 1:
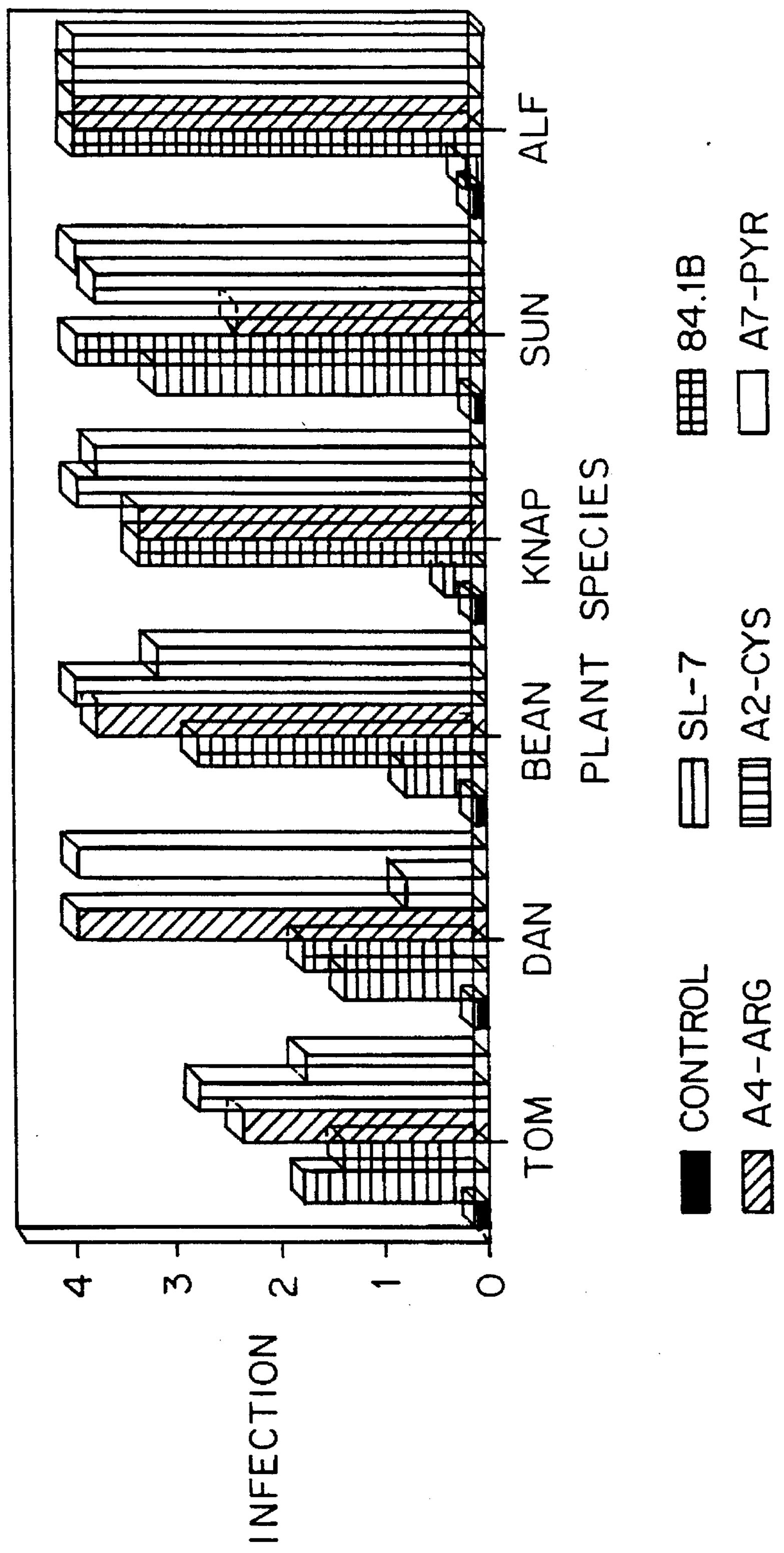
FIG. 1 illustrates results of greenhouse test for virulence of mutant strains of *S. sclerotiorum.*

This invention arose from the desire to obtain improved biological herbicide agents having highly lethal characteristics (broad spectrum) with respect to weeds and either (1) a limited survival time (biological half life) and geographical dissemination characteristics, or a (2) limited herbicidal activity towards beneficial plant species (specificity limited plant spectrum). In the latter case, the preferred result is to preserve the weed killing capability of the mutant as broadly as possible and yet limit the beneficial plant species spectrum of the agent.

The microbial herbicides according to the invention, whose limiting characteristics are clearly characterized, are specifically characterized in terms of a reproducible product-by-process procedure, which results in the production and isolation of microbial herbicides having the clearly stated limiting characteristics of the herbicidal agents according to the invention. The parameters for producing the bioherbicides according to the invention and the criteria for isolating the bioherbicides having the desired characteristics (by the described procedures, which can readily preformed by one of ordinary skill in the art without undue experimentation) are clearly described in the specification which follows.

One of ordinary skill in the art following the guidance of the invention's description below will be able to visualize and produce bioherbicides meeting the characteristics required for bioherbicides according to the invention.

Biological herbicides, as disclosed herein, have the advantage over chemical herbicides and other non-mutagenized biological herbicides in not persisting in the environment. However, limited knowledge of host specificities among plant pathogens has been a deterrent in the past to the development of biological herbicides in general.

Because of the potential destruction from biological herbicides, previous efforts at producing bioherbicides have been limited to obtaining narrow spectrum bioherbicides. This was necessary because in the event the biological herbicides were released into the environment because they could potentially destroy crops which are nearby, next year's crops, or reproduce and remain dormant to create destruction at a later date. Thus, much effort has been expended to obtain that which has been thought of as the ideal bioherbicide to resolve the above problems i.e., a bioherbicide that is specific for one host (one plant) against which it is very destructive but harmless to all other plants. As can be appreciated, obtaining such a narrow host range bioherbicide specific for only a particular non-beneficial plant host is extremely difficult. Mutations to plant pathogens are seldom so specific as to produce a host specific pathogen which is harmless to all other plants. Naturally, reproducing such results would also be very difficult unless the resulting microorganism were well preserved and well characterized.

The present invention radically departs from the traditional idea of obtaining a "narrow spectrum" bioherbicide. The present invention resolves the problems in the prior art of potential destruction caused by persistence of the plant pathogens.

Applicants have discovered that the broad spectrum capability of the herbicide can be maintained such that a wide variety of pathogens can be destroyed, and yet have resolved the problem of pathogen persistence to harm other plants. Applicants have resolved the prior art problems by limiting the period of time the bioherbicide can exist. Two ways in which this is done is by (1) reducing the ability of the organism to produce spores or other life forms capable of long term survival, or (2) modifying the bioherbicide so that the bioherbicide requires an essential nutrient not normally available in the environment where it will be used (i.e., in a "wild-type" environment). For example, in the latter situation "(2)" referred to above, the bioherbicide is applied along with a limited amount of the essential nutrient such that the bioherbicide will be unable to reproduce and infect a plant after the essential nutrient is completely consumed by the growing bioherbicide.

The biological herbicides of the invention are completely destructive to the weed host if their application is timed to take advantage of particularly favorable weather conditions which coincide with the agricultural season. Once applied, the biocide is effective for controlling weeds for a limited period of time. In some cases, the biocidal herbicide will not survive the harsher conditions of the winter season in most agricultural areas. Other types of self-delimiting mutants will not persist for a prolonged period of time, e.g., due to their reduced ability to produce spores or other life forms capable of long-time survival, and the like. For example, with the bioherbicides which are unable to survive the harsh winter conditions of a particular environment, the bioherbicides can be broad spectrum enough to be pathogenic to beneficial plants since they can be applied at the end of the growing season of the beneficial plants. In that case, most or all of the plants in a particular area can be destroyed by a single application and the bioherbicide will not survive the winter to interfere with beneficial plants which will be planted the following spring. Thus the use of bioherbicides according to the present invention has the extremely beneficial advantage of eliminating the necessity of using broad spectrum chemical herbicides to prepare an area for agriculture use, which chemical herbicides have a well-known tendency to persist in the environment and pollute it.

A variety of weeds which are fast growing and troublesome for crop raising are common in agricultural fields of the United States. They may reduce the yield, quality, or both, of the crops or plants. The effect of the weeds is attained by a variety of means, including competition for nutrients, shading of the plants and the like.

Although the concept of biological control of weeds has been known, the literature is sparse when it comes to pathogenic mutants useful for weed control. As described above, the present invention is based on a new approach relying on mutagenesis of known organisms followed by selection of specific strains having either reduced lethality to beneficial plants or environmental suitability when compared with the wild type organism. This approach will result in a dramatic increase in the number of organisms for use as biological herbicidal agents. In general it can be said that the approach utilized herein can be applied to any microorganism which is highly effective in killing weeds.

Mutagenesis is used with known organisms to produce the biological herbicidal agents according to the present invention. The term mutagenesis, as it is used in the present specification previously and throughout, is defined as follows. The mutagenesis of the known organisms is done by use of methods such as exposure to UV light or exposure to chemical agents which cause the known organisms to mutate. For example, known organisms are exposed to UV light to reduce the number of live organisms to less than about 5% of the initial number, which destroys or changes some of the genetic material in some of the remaining organisms that are not killed. Optionally, the organisms can be photosensitized by placing them in contact with agents such as 8-methoxy-psoralen for about 90 minutes prior to exposure to the UV light. Moreover, the remaining 5% of the organisms can be exposed to longer wavelength UV light. Following the mutagenesis procedure, the organisms which are not destroyed by the UV light can be cultured and screened for desired traits.

Additionally, mutants can be produced via chemical mutagenesis rather than UV light. Chemical agents such as 1-methyl-3-nitro-1-nitrosoguanidine (NTG) or acridine for about 120 to 300 minutes. The organisms can then be washed of the chemical mutagenic agent, cultured, and screened for the desired traits.

Plant pathogenic fungi can be efficiently utilized as a microorganism for the biological herbicidal agent.

Examples of acceptable plant pathogenic fungi useful in the present invention are generally classified in five main groups under the division of Eumycota. These groups are Mastigomycotina, Zygomycotina, Ascomycotina, Basidiomycotina, and Deuteromycotina. Preferred are fungi from the subdivision Basidiomycetes, and particularly preferred are Sclerotinia and Rhizoctonia.

Fungi are microorganisms that contain no chlorophyll, which usually reproduce by producing spores. Although sometimes classified as simple plants, they have no roots, stems or leaves and are now placed in a kingdom of their own, Mycetae. The fungi are considered a unique group of organisms distinct from bacteria, animals and plants. Fungi include yeast, a single celled organism, and the other fungi which grow as colonies (in groups). Fungi are a very old group of microorganisms which have been on the earth for more than two billion years. Spores of plant pathogenic fungi having been found in the burial chambers of pyramids on ancient grains. Examples of fungi are yeast, mushrooms, toadstools, molds, and mildews.

The body or vegetative stage of a fungus comprises branching, delicate, thread-like structures called hyphae. When many hyphae are interlaced into a tangle there known as mycelium (the plural of which is mycelia). All fungi are capable of breaking down complex organic foods into simple substances and using these substances as sources of energy.

There are about 8,000 species of fungi which can cause plant diseases and all plants are attached by some fungi. Even though some fungi attack many species of plants, others attack only one type of plant. Many fungi reproduce by forming spores at the ends of, inside, or on specialized hyphae and structures. These spores are tiny, microscopic bodies the size of dust, and are produced in huge numbers.

The function of spores is similar to that of seeds and higher plants since they are carried by the wind, water and other objects or animals to a new host. In some fungi, the mycelium can pass into a dormant or resting stage by forming closely compacted hyphae, known as sclerotia. Sclerotia can vary in size from only a few cells (microsclerotia) up to many thousands of cells. Most sclerotia are quite small but some can be very large. By forming sclerotia, fungi can effectively hibernate and survive through conditions which would otherwise be unfavorable for growth, such as cold, drought, heat, or the absence of a plant host. When favorable conditions return, sclerotia can then form hyphae to infect the host, form a new mycelium or produce a reproductive body of some sort (for example, spores to cause a wide dissemination).

For some species which do not produce sclerotia. the spore stage is the procedure which these fungi use to pass the winter or unfavorable conditions and thus the spore becomes a resting spore. Because spores are of so many different kinds, they will be different in color, size, structure and wall thickness. Spores need certain temperatures and moisture conditions to germinate and grow. Few spores will germinate when it is very cold, with the optimum temperature for germination of most spores between 15° C. and 25° C.

There are 5 main groups of plant-pathogenic fungi, differentiated for the most part by their hyphae characteristics and how they reproduce. The major groups or sub-divisions of fungi, under the division Eumycota (or true fungi), are the Mastigomycotina, Zygomycotina, Ascomycotina, Basidiomycotina, and Deuteromycotina.

Within the above sub-divisions the fungi are often referred to with the prefix preceding mycotina taken with the word mycetes, e.g., Basidiomycetes for Basidiomycotina. Some plant pathogenic fungi may also occur in a division of fungi known as Myxomycota.

A particularly important division of fungi is Basidiomycotina, which include the genus Sclerotinia and the division Dueteromycotina which includes the genus Rhizoctonia (example *Rhizoctonia solani*). Some fungi have two scientific names, one for the asexual stage or the anamorph and the other for the sexual stage.

In general, plant diseases caused by fungi can be classified into two major types: those caused by airborne-fungi and those caused by soil-borne fungi.

The concept of the present invention is operable with any plant pathogen, but particular emphasis is placed upon deriving pathogens which will not produce spores and/or sclerotia. These plant pathogens are usually fungi. Such species are not able to winter over, survive periods of drought or times when a host is unavailable. The survival of such adapted pathogens requires an environment where the pathogen can continue to grow under proper moisture, temperature, and nutrient conditions.

Another limitation option is to require the microorganism to be unable to grow in the wild type environment without being supplemented with a specific nutrient. Such a fastidious nutrient requirement requires applying both the pathogen and the nutrient to an area before the plant pathogen will grow and harm the plant host. Once the nutrient is used up, the pathogen loses the ability to infect the host. The pathogen will either die or go into a dormant stage. It is still harmless in a dormant stage since the required nutrient is absent in the wild type environment. A particular advantage for a fastidious bioherbicide is a species which produces either spores or sclerotia, when the fastidious nutrient (not normally present in the wild-type environment) is used up.

Thus, reapplying the bioherbicide at a later desired time is unnecessary; only a predetermined amount of the fastidious nutrient need be applied to re-activate the biocidal activity of the bioherbicide.

The invention will now be described in relationship to particular types of non-limiting plant pathogen fungi, which may be used in the present. invention. As described above, any plant pathogen can be modified using the present invention method. One particular microorganism, *Sclerotinia sclerotiorum* is present in many of the examples; but the same methods and information are applicable to other plant pathogens, and particularly to pathogenic fungi.

*Sclerotinia sclerotiorum* was found to be effective in killing a variety of weeds including Canada thistle (*Cirsium arvense* (L.) Scop.), spotted knapweed (*Centaurea macculosa* Lam.), and has been reported to attack species of weeds in over forty different genera. *S. sclerotiorum* is also known to kill a large variety of weeds in a matter of days under greenhouse conditions and in a few weeks in the field under standard agricultural conditions. These are excellent characteristics which make any microorganism, and particularly *S. sclerotiorum,* a good candidate for obtaining mutants useful as a biological herbicide.

To its detriment, *S. sclerotiorum* is also known to attack a number of beneficial native plants and crops. This clearly limits its use making it practically unsuitable for application to cultivated areas or areas containing native plants or trees.

In one aspect of the invention, there is provided a broad spectrum bioherbicide comprising a mammal-sparing broad bioherbicide fungal mutant having substantially limited survival time and geographical dissemination characteristics under standard agricultural conditions. This mutant has at least one altered characteristic, such as phenotype or morphology when compared with the wild type. An example of an altered characteristic mutant is one being substantially incapable of producing sclerotia or ascospores. Similarly, a mutant having an altered phenotype may be one having an inability of surviving adverse temperatures or other adverse environmental conditions, among others. The morphology of the mutant may be altered with respect to the wild type in terms of pigmentation, mycelial habits such as density, area, growth rate and the like, survival structures such as sclerotia or reproductive structures, among others.

In general, the phenotypic differences exhibited by the mutant with respect to the wild type bioherbicide fungus may be an increased susceptibility to an environmental condition such as temperature, soil conditions, chemicals and the like. Another phenotypic difference may be an auxotrophy which is nonexistent in the wild type. Thus, the mutant will require a certain nutrient in the medium without which it will not be capable of growth whereas such requirement was not a characteristic of the wild type microorganism.

In the case of the above-described *S. sclerotiorum* mutant, the broad spectrum bioherbicides described in the examples, e.g, Al-Pyr and SL-1, do not show reduced plant spectra with respect to the wild type. They are however limited in terms of their survival time and the area over which they can disseminate. The aim is to have this type of biological herbicide kill as many weeds as it can over a short period of time and then disappear from the environment. Typically, such a bioherbicide can be utilized in the preparation of a field for agricultural cultivation although other uses are also possible.

The broad spectrum biocide described above is also provided as a biocidal composition containing an agriculturally acceptable carrier. Suitable liquid and solid carriers are known in the art and need not be described herein.

Specific *S. sclerotiorum* mutants disclosed herein having the characteristics described above and identified by the names Al-PYR and SL-1 are presently deposited with the Department of Plant Pathology at Montana State University in Bozeman, Montana. Cultures of these mutants will be deposited with the American Tissue Culture Collection of Rockville, Md., USA, prior to the issuing of a patent on this invention.

Mutant microorganisms as those described above are prepared by obtaining viable wild type microorganism spores, e.g., *S. sclerotiorum* spores, subjecting the spores to the rays of ultraviolet (UV) light under conditions effective to reduce the number of viable spores to less than about 5% the initial number, selecting mutants which differ from the wild type in at least one characteristic such as altered phenotype or morphology (e.g., inability to produce ascospores or sclerotia), and further selecting a mammal-sparing herbicidal mutant having substantially reduced survival time and geographical dissemination characteristics under standard agricultural conditions when compared with the wild type microorganism.

The spores may be placed in a growth medium prior to contacting them with the UV light. Typically, the spores may be suspended in sterile distilled water and placed on a growth medium such as potato dextrose agar (PDA). However, other media are also suitable. Conditions for culturing the ascospores are known in the art.

Typically, the spores are subjected to light in the ultraviolet range, e.g. about 254 to 300 nm for about 60 seconds to 300 minutes or more. The exposure to UV light may be conducted repeatedly if necessary to attain a high level of destruction of the ascospores.

When the number of spores is below about 5% the initial number, the spores are grown in a growth medium, and microorganism mutants are selected by testing for altered phenotype or morphology utilizing means known in the art. The mutants may be observed under the microscope for any visible changes in the morphology, e.g., pigmentation, size, shape, colony formation and the like. The search for altered phenotype is conducted by subjecting the UV irradiated culture to different conditions including different temperatures, auxotrophy, medium compositions, humidities and the like, and observing if any growth occurs which was not noticed under the growth conditions of the wild type.

Once a mutant is obtained as indicated above it is tested under standard agricultural conditions to ensure that it does actually have reduced survival time and geographical dissemination characteristics when compared with the wild type. In the context of this invention standard agricultural conditions mean the application and growth of the mutant microorganisms during cultivation and harvest times and the death of the microorganisms during the harsher winter months in areas of the U.S.A.

In a particular embodiment of the invention the spores may be photosensitized by contacting them with a UV sensitizing agent prior to the UV treatment. UV sensitizing agents are known in the art and need not be listed herein. An example of a preferred UV sensitizing agent is 8-methoxypsoralen. The spores may be exposed to about 80 to 120 micrograms/ml 8-methoxypsoralen for about 60 to 120 minutes. Other UV sensitizing agents may be utilized in different concentrations and for different periods of time as is known in the art.

After selection the mutants can be grown under favorable conditions and stored at temperatures below about 4° C.

Also part of the invention is a method of reducing the number of weeds in an area while sparing mammals and permitting the cultivation of said area at a later time. The method comprises applying to the weeds or the area a weed biocidal amount of an inoculum of a mammal-sparing bioherbicide fungal mutant having substantially reduced survival time and geographical dissemination characteristics under standard agricultural conditions when compared with the wild type.

The microorganism mutants may be utilized by simple application to the weeds or the sites around the weeds or in general to an area which is prepared for future cultivation. The mutants may be applied over a broad range of densities per plant or area of soil. Preferred are ranges of at least about 1 to $10^8$, and more preferably about 10 to $10^2$ mutants per weed. Carriers suitable for use herein are those which are typically utilized in the art, some of which were described above. Solid carriers may also be utilized herein.

EXAMPLES

Example 1

Mutagenesis of *S. sclerotiorum* ascospores

Ascospores of *S. sclerotiorum* were obtained from apothecia formed on axenic vernalized sclerotia placed on water agar. The ascospores were discharged into sterile distilled water and placed on potato dextrose agar (PDA) . The ascospores were mutagenized by exposure to 254 nm UV light to reduce the number of viable ascospores to less than about 5% the initial number.

Example 2

Second Method of Mutagenizing *S. sclerotiorum* ascospores.

*S. sclerotiorum* ascospores were obtained from apothecia formed on axenic vernalized sclerotia and were placed on water agar. Thereafter the ascospores were discharged into sterile distilled water and placed on PDA. The ascospores were then photosensitized after being collected on a 0.22 micron membrane filter. The ascospores were photosensitized by placing them in contact with 100 micrograms/ml 8-methoxypsoralen for ninety minutes. Thereafter the photosensitized ascospores were exposed for 60 seconds to UV light of 254 nm and then for 300 minutes to UV light of 300 nm.

Selection for Different Phenotype or Morphology or Altered Host Range

Approximately 1,100 mutagenized ascospore-derived isolates are tested for auxotrophy, altered colony morphology and altered host range.

Example 2A

Method of Chemically Mutagenizing *S. sclerotiorum*

Additional mutants were produced via chemical mutagenesis rather than by using ultra-violet light. Wild-type isolates of *S. sclerotiorum* were cultivated in submerged cultures in 50 ml potato dextrose broth (Difco) in 250 ml Erlenmeyer flasks, agitated at 250 rpm's on a rotary shaker at room temperature. The mycelium was exposed to either 50 μg/ml 1-methyl-3-nitro- 1-nitrosoguanidine (NTG) for 180 minutes or to 50 μg/ml acridine mutagen ICR-170 for 150 minutes. The mutagenized mycelium was collected via filtration Miracloth (CalBiochem), washed three times with sterile distilled water, and placed in fresh sterile potato dextrose broth for 36 hours. The mycelium was then subjected to protoplasing using Novozyme 234 and β-glucuonadase for 4 hours. The protoplasts were regenerated in liquid broth containing 1M sorbitol for 12 hours and then spread onto potato dextrose agar.

Selection for Different Phenotype or Morphology or Altered Host Range

Individual regenerated protoplasts that successfully developed colonies were then subjected to nutritional and sclerotia-production analyses to test for auxotrophy and altered colony morphology. Confirmed new auxotrophs non-sclerotial isolates were then subjected to virulence testing in the greenhouse to test for altered host range.

Example 3

Selection for Altered Auxotrophy and Morphology

Mycelial agar plugs of mutated fungal cultures were placed in a minimal agar medium and onto minimal medium supplemented with yeast extract. Mutant isolates that grew on supplemented medium, but failed to grow on the minimal agar medium were considered indicative of auxotrophy and were subsequently analyzed for their particular nutritional requirement. The isolates were also observed for alterations in colony morphology including an inability of forming sclerotia, pigmentation and alterations in mycelial habits such as density, area and growth rate.

Example 4

Test for Pathogenicity

Pathogenicity tests were conducted on 9 hosts:

*Centaurea maculosa* Lam. (spotted knapweed),

*Cirsium arvense* (L.) Scop. (Canada thistle),

*Brassica napus* L. (rape),

*Carthamus tinctorus* L. (safflower),

*Helianthus annuus* L. (sunflower),

*Lactuca sativa* L. (lettuce),

*Lens culinaris* Medik (lentil),

*Phaseolis vulgaris* L. (bean), and

*Trifolium hybridum* L. (clover).

Mycelial agar plugs or infested millet inocula were placed on the bases of test plants. Auxotrophs require nutrient supplementation to the inoculation site in order to incite disease. One such example is the auxotroph mutant obtained in Example 1 above. Thereafter the test plants were assessed for pathogen attack 7 to 10 days after inoculation.

CHARACTERISTICS OF THE *S. SCLEROTIORUM* MUTANTS OBTAINED

Example 5

Isolation and Characterization of the mutant *S. sclerotiorum* Al-Pyr Mutant It was found that an isolated mutant requiring nutrients that are not required by the wild type fungus retains its auxotrophic character over subsequent generations. The nutritional requirement of this auxotroph was found to be pyrimidines and more specifically cytosine. The isolate did not grow on minimal medium or medium containing thymidine. It grew very slowly on medium containing 50 micrograms/ml uracil and rapidly on medium containing 50 micrograms/ml cytosine. Al-Pyr exhibited only 20% maximum infestation of millet in the absence of cytosine supplement. A supplement of 30 mg/kg of cytosine increased millet infestation to 90%.

The Al-Pyr mutant did not show reversions during numerous laboratory transfers and resulting generations of fungi. In addition all ascospores from the mutant retained their cytosine requirement. Apothecial stipes formed on axenic sclerotia of the isolate. However, cytosine was required for the stipes to complete apothecial maturation.

Example 6

Virulence of the *S. sclerotiorum* Al-Pyr Mutant

Only an occasional plant developed a lesion when Al-Pyr was inoculated as mycelial agar plugs. However, inoculation of plants with Al-Pyr and an aqueous solution of 2 g/l yeast extract or 50 mg/l cytosine resulted in lesions on all the plants. Of the remaining plants except beans, which are highly lignified and develop only lesions during the short testing time, approximately 25% of the plants treated with the yeast extract and the Al-Pyr mutant and over 85% of the plants treated with cytosine and the Al-Pyr mutant died over the course of the test period.

As indicated supra millet inoculum requires 30 mg/kg cytosine to achieve 90% infestation. This cytosine level also allows attack of some plants:

0% of beans,

10 % rape,

20% sunflowers,

30% lentils, and over 50% clover, lettuce and safflower.

Addition of 10 to 30 mg/kg cytosine to the Al-Pyr resulted in death of over 80% of all plants but beans.

Example 7

Isolation, Characterization and Pathogenicity of *S. sclerotiorum* SL-1

An ascospore obtained in Example 2 failed to produce sclerotia on the medium. This particular mutant was incapable of producing ascospores and therefore incapable of aerial dissemination since apothecia form on the sclerotia. In addition, this mutant is not expected to survive the winter months in temperate or cooler invironments since sclerotia also serve as the survival structure for the fungus.

The non-sclerotial form was segregated away from the sclerotia-forming sectors by hyphal tipping. Subsequently, SL-1 has never been observed to produce sclerotia in laboratory cultures, on grain or on infected plants. Colonies of this fungus formed more dense mycelia and grew at slower rates than the parental wild type fungus. The SL-1 mutant isolate can be used in a manner analogous to a broad-spectrum herbicide while sparing mammals and other organisms because it killed many plant species in the area of application. *S. sclerotiorum* SL-1 retained its pathogenicity at levels comparable to the wild type as can be seen from the data in Table 1.

TABLE 1

*S. sclerotiorum* SL-1 pathogenicity

| Host | Number of plants killed* by | |
|---|---|---|
| | Wild-type fungus | Mutant (SL-1) |
| Spotted knapweed | 5 | 3 |
| Bean | 4 | Lesions |
| Lettuce | 4 | 5 |
| Lentil | 5 | 5 |
| Rape | 5 | 3 |
| Safflower | 4 | 2 |
| Sunflower | 5 | 5 |

*Total Number of plants tested: 5.

EXAMPLE 8

Field Trials

Field trials have been conducted with both wild type and the *S. sclerotiorum* Al-Pyr, SL-1 and HR-1 mutants of the fungus. The fungi were routinely grown on potato dextrose agar. The field inoculum consisted in each case of sterile millet infested with one variety of fungus. The millet was prepared by imbibing the grain for 16 hours in distilled water, draining excess water and autoclaving at 121° C. for one hour.

For *S. sclerotiorum* Al-Pyr (an auxotroph mutant) imbibition was done with a nutrient solution containing either yeast extract or cytosine rather than water. The sterile millet was then inoculated with a mycelial agar plug of the fungus and allowed to ramify throughout the millet for about 10 days. The infested millet was dried at 27° C. and stored at 4° C.

Prior to its use the inoculum was coated with 10 wt % corn or safflower oil to promote growth and reduce desiccation. The inoculum was then applied by distributing it upon the area, i.e., broadcasting.

Experimental field trials with wild type isolates of *S. sclerotiorum* resulted in maximum reductions of over 80% of populations of Canada thistle and spotted knapweed. The effectiveness of the fungus was dependent on the particular isolate, time of application, prevailing weather conditions and inoculum quality.

Also in experimental field trials approved by the U. S. Environmental Protection Agency with the three mutants *S. sclerotiorum* Al-Pyr, SL-1 and HR-1, no mutants are re-isolated from treated plants after the winter months. This indicated that none of the mutants survived the winter.

The mutants produced in accordance with the invention, *S. sclerotiorum* Al-Pyr, SL-1 and HR-1 are on deposit in the Plant Pathology Department Fungal Collection under the direction of Mr. Don Mathre, Curator, at Montana State University, Bozeman, Mont. The microorganisms will be maintained on deposit at Montana State University in viable form until at least the date an indication is received that this patent application contains allowable subject matter. Subsequent to that time and prior to the issuing of a patent the deposited microorganisms will be transferred to a public depository, the American Type Culture Collection and maintained permanently therein.

Example 9: Isolation and Characterization of the *S. sclerotiorum* A4-ARG Mutant The procedures and examples 2A and 3 were followed and a *S. sclerotiorum* A4-ARG mutant was isolated that required a nutrient which was not required by the wild type fungus and which retained its auxotrophic character over subsequent generations. The nutritional requirement of this auxotroph was found to be an amino acid and, more specifically, arginine. The A4-ARG mutant does not show reversions during numerous laboratory transfers in resulting generations of fungi. In addition, all ascospores from the mutant retained their arginine requirement.

Example 10

Isolation and Characterization of the *S. sclerotiorum* A5-LYS

The procedures and examples 2A and 3 were followed and a *S. sclerotiorum* A5-LYS mutant was i solated that required a nutrient which was not required by the wild type fungus and which retained its auxotrophic character over subsequent generations. The nutritional requirement of this auxotroph was found to be an amino acid and, more specifically, lysine. The A5 -LYS mutant did not show reversions during numerous laboratory transfers in resulting generations of fungi. In addition, all ascospores from the mutant retained their lysine requirement.

Example 11

Isolation and Characterization of the *S. sclerotiorum* A6-ARG Mutant

The procedures and examples 2Aand 3 were followed and a mutant A6-ARG was isolated that required a nutrient which was not required by the wild type fungus and which retained its auxotrophic character over subsequent generations. The nutritional requirement of this auxotroph was found to be an amino acid and, more specifically, arginine. The A6-ARG mutant did not show reversions during numerous laboratory transfers in resulting generations of fungi. In addition, all ascospores from the mutant retained their arginine requirement.

Example 12

Isolation and Characterization of the *S. sclerotiorum* A8-LEU

The procedures and examples 2A and 3 were followed and a mutant A8-LEU was isolated that required a nutrient which was not required by the wild type fungus and which retained its auxotrophic character over subsequent generations. The nutritional requirement of this auxotroph was found to be an amino acid and, more specifically, leucine. The A8-LEU mutant did not show reversions during numerous laboratory transfers in resulting generations of fungi. In addition, all ascospores from the mutant retained their leucine requirement.

Example 13

Isolation and Characterization of the *S. sclerotiorum* A13-LYS Mutant

The procedures and examples 2A and 3 were followed and a mutant *S. sclerotiorum* A13-LYS was isolated that required a nutrient which was not required by the wild type fungus and which retained its auxotrophic character over subsequent generations. The nutritional requirement of this auxotroph was found to be an amino acid and, more specifically, lysine. The Al3-LYS mutant did not show reversions during numerous laboratory transfers in resulting generations of fungi. In addition, all ascospores from the mutant retained their lysine requirement.

Example 14

Isolation and Characterization of the *S. sclerotiorum* A14-ISO/VAL Mutant

The procedures and examples 2A and 3 were followed and a mutant A14-ISO was isolated that required a nutrient which was not required by the wild type fungus and which retained its auxotrophic character over subsequent generations. The nutritional requirements of this auxotroph were found to be amino acids and, more specifically, isoleucine and valine. The Al4-ISO/VAL mutant did not show reversions during numerous laboratory transfers in resulting generations of fungi. In addition, all ascospores from the mutant retained their isoleucine and valine requirement.

Example 15

Isolation, Characterization and Pathogenicity of the *S. sclerotiorum* SL- 7 Mutant Another isolate obtained in Example 2A failed to produce sclerotia on the medium. This particular mutant was incapable of producing ascospores and therefore incapable of aerial dissemination since apothecia form on the sclerotia. In addition this mutant was not expected to survive the winter months in most temperate or cooler environments since sclerotia also serve as the survival structure for the fungus.

The non-sclerotial form was segregated away from the sclerotia-forming sectors by hyphal tipping. Subsequently, SL-7 has never been observed to produce sclerotia in laboratory cultures, on grain or on infected plants. Colonies of this fungus formed more dense mycelia and grow at slower rates than the parental wild type fungus. The SL-7 mutant isolate can be used in a manner analogous to a broad-spectrum herbicide while sparing mammals and other organisms because it killed many plant species in the area of application. SL-7 retains pathogenicity at levels comparable to the wild type.

Example 16

Method of Chemically Mutagenizing *S. rolfsii*

Additional mutants are produced via chemical mutagenesis rather than ultra-violet light. Wild-type isolates of and *S. rolfsii* are cultivated in submerged cultures in 50 ml potato dextrose broth (Difco) in 250 ml Erlenmeyer flasks, agitated at 250 rpm's on a rotary shaker at room temperature. The mycelium is exposed to either 50 μg/ml 1-methyl-3-nitro-1-nitrosoguanidine (NTG) for 180 minutes or to 50 μg/ml acridine mutagen ICR-170for 150 minutes. The mutagenized mycelium are collected via filtration Miracloth (CalBiochem), washed three times with sterile distilled water, and placed in fresh sterile potato dextrose broth for 36 hours. The mycelium is then subjected to protoplasing using Novozyme 234 and β-glucuonadase for 4 hours. The protoplasts are regenerated in liquid broth containing 1M sorbitol for 12 hours and then spread onto potato dextrose agar.

SELECTION FOR DIFFERENT PHENOTYPE OR MORPHOLOGY OR ALTERED HOST RANGE

Individual regenerated protoplasts that successfully develop colonies are then subjected to nutritional and sclerotia-production analyses to test for auxotrophy and altered colony morphology. Confirmed new auxotrophs non-sclerotial isolates are then subjected to virulence testing in the greenhouse to test for altered host range.

Example 19

Selection for Altered Auxotrophy and Morphology.

Mycelial agar plugs of mutated fungal cultures are placed in a minimal agar medium and onto minimal medium supplemented with yeast extract. Mutant isolates failing to grow on the minimal agar medium are indicative of auxotrophy and are subsequently analyzed for their nutritional requirement. The isolates are also observed for alterations in colony morphology including an inability of forming sclerotia, pigmentation and alterations in mycelial habits such as density, area and growth rate.

Example 18

Test for Pathogenicity

Pathogenicity tests are conducted on 9 hosts:

*Centaurea maculosa* Lam. (spotted knapweed),

*Cirsium arvense* (L.) Scop. (Canada thistle).

Mycelial agar plugs or infested millet inocula are placed on the bases of test plants. Auxotrophs require nutrient supplementation to the inoculation site in order to incite disease. Thereafter the test plants are assessed for pathogen attack 7 to 10 days after inoculation.

CHARACTERISTICS OF THE *S. ROLFSII* MUTANTS OBTAINED

Example 19

Isolation and Characterization of the Mutant *S. rolfsii* A27-Pyr Mutant

It is found that an isolated mutant requiring nutrients that are not required by the wild type fungus retains its auxotrophic character over subsequent generations. The nutritional requirement of this auxotroph is found to be pyrimidines and more specifically cytosine. The isolate does not grow on minimal medium or medium containing thymidine. It grows very slowly on medium containing 50 micrograms/ml uracil add rapidly on medium containing 50 micrograms/ml cytosine. *S. rolfsii* A27-Pyr exhibits only about 20% maximum infestation of millet in the absence of cytosine supplement. A supplement of about 30 mg/kg of cytosine increases millet infestation to 90%.

The A27-Pyr mutant does not show reversions during numerous laboratory transfers and resulting generations of fungi. In addition all ascospores from the mutant retain their cytosine requirement. Apothecial stipes formed on axenic sclerotia of the isolate. However, cytosine is required for the stipes to complete apothecial maturation.

Example 20

Isolation and Characterization of the *S. rolfsii* A28-ARG Mutant

The procedure similar to that of Example 2 is followed and a *S. rolfsii* A28-ARG mutant is isolated that required a nutrient which is not required by the wild type fungus and which retains its auxotrophic character over subsequent generations. The nutritional requirement of this auxotroph is an amino acid and, more specifically, arginine. The A28-ARG mutant does not show reversions during numerous laboratory transfers in resulting generations of fungi. In addition, all ascospores from the mutant retain their arginine requirement.

Example 21

Isolation and Characterization of the *S. rolfsii* A29-LYS

The procedure similar to that of Example 2 is followed and a *S. rolfsii* A29-LYS mutant is isolated that requires a nutrient which is not required by the wild type fungus and which retains its auxotrophic character over subsequent generations. The nutritional requirement of this auxotroph is an amino acid and, more specifically, lysine. The A29-LYS mutant does not show reversions during numerous laboratory transfers in resulting generations of fungi. In addition, all ascospores from the mutant retain their lysine requirement.

Example 22

Multiple Geographic Field Trials

Treatment tests were conducted on turf plots in Montana, Kentucky, and New Zealand, which plots were infested with a diversity of weeds including, depending upon the location: dandelion, buttonweed, mock s trawbeery, dicondra, white clover plantain, spoted knapweed, and Canada thistle. Both wild-type *S. sclerotiorum* and mutants of *S. sclerotiorum* were tested. This demonstrated the efficacy of the mutants in different environments against a diversity of weeds. The mutant strains tested achieved up to 80 percent control as compared with up to 90 percent control for the wild-type fungus. This means that the mutants are only slightly less effective than the wild-type in field trials.

Detailed Description of FIGS. 1–9

FIGS. 1–8 show the results of various mutants and wild-type species of *S. sclerotiorum* in greenhouse or field trial tests. FIG. 9 shows the comparative field trial efficacy results of several formulations having a wild-type *S. sclerotiorum* species as the active ingredient. The figures are specifically described as follows.

FIG. 1 illustrates results of greenhouse tests for virulence of mutant strains of *S. sclerotiorum* A2-CYS, A4-ARG, A7-PYR, and SL-7 as compared to wild type *S. sclerotiorum* 84.1B and a inactive control. The plants tested against were tomato, dandelion, bean, spotted knapweed, sunflower, and alfalfa plants.

Figure 2:
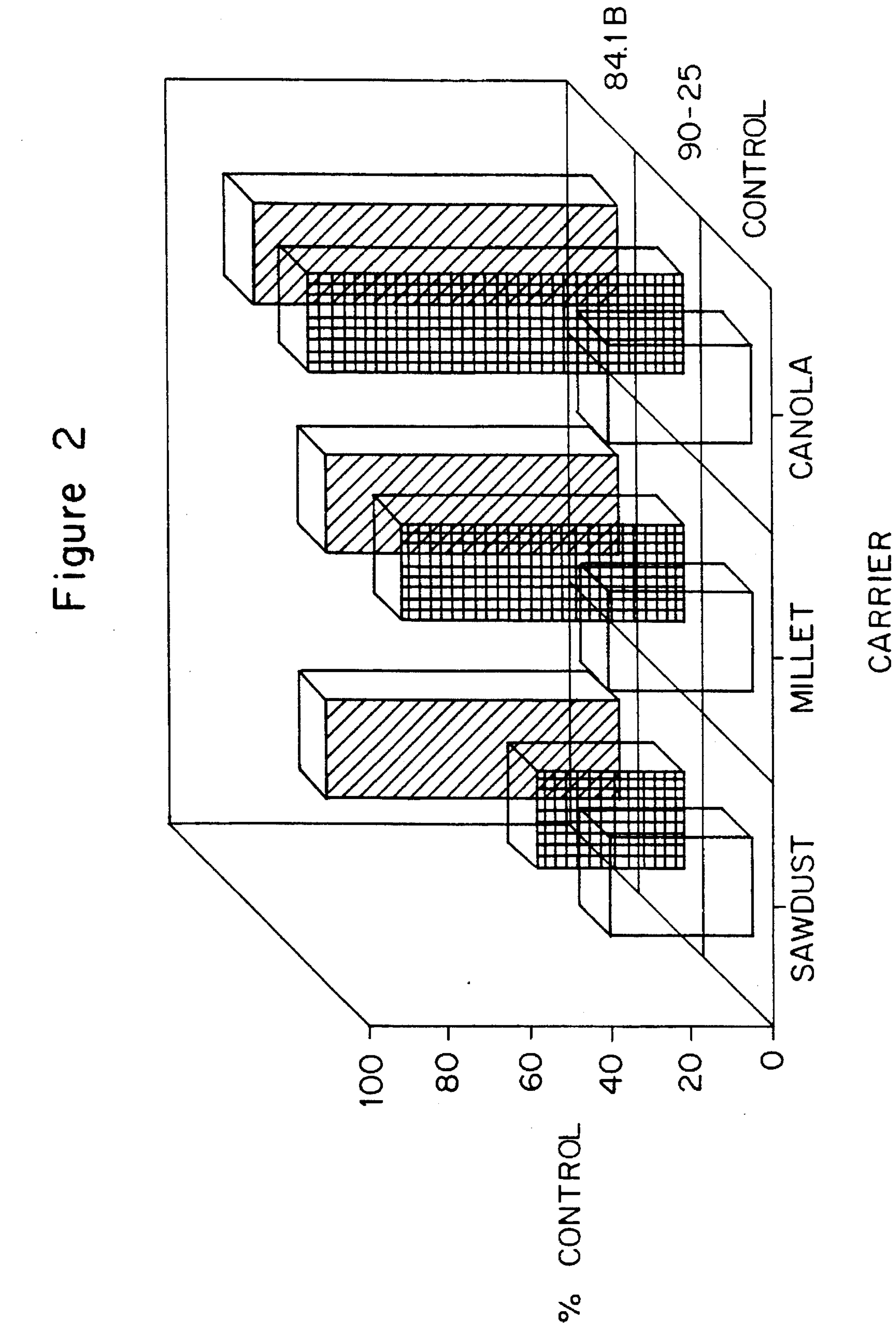
FIG. 2 illustrates the relative efficacy of wild-type isolates of *S. sclerotiorum* (species 84.1B and 90-25) on dandelion.

FIG. 2 illustrates the relative efficacy of wild-type isolates of *S. sclerotiorum* (species 84.1B and 90-25) on dandelion as compared to an inactive control. Formulations having effective amounts of each of these two wild-type species in sawdust, millet, and canola and a contol of each with no active ingredient were compared for efficacy.

Figure 3:
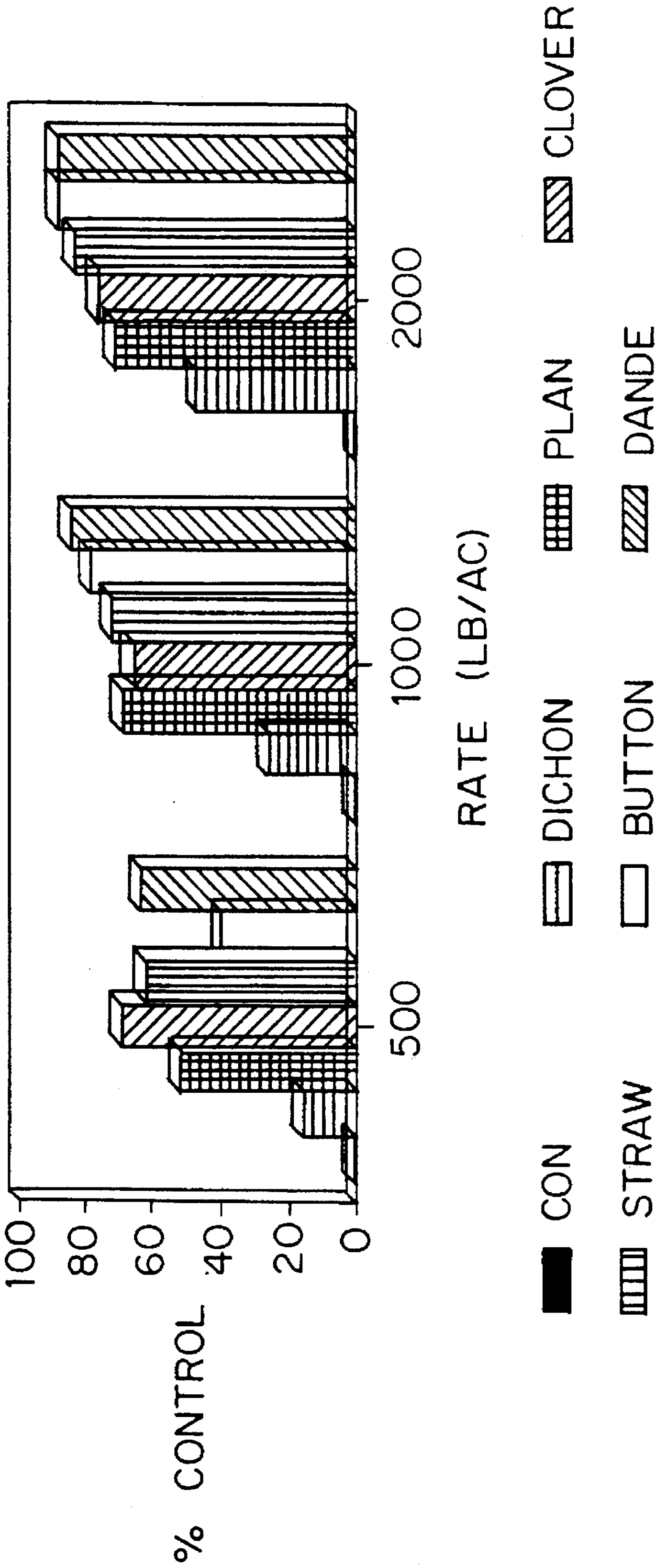
FIG. 3 illustrates the efficacy of wild-type strain *S. sclerotiorum* 84.1B after 10 days.

FIG. 3 illustrates the efficacy of wild-type strain *S. sclerotiorum* 84.1B against several varieties of plants after 10 days. Also, compared were the application rates of 500, 1000, and 2000 pounds of active ingredient per acre. The plant species tested against as shown in this figure are control, dichondra, plantain, white clover, mock strawberry, buttonweed, and dandelion.

Figure 4:
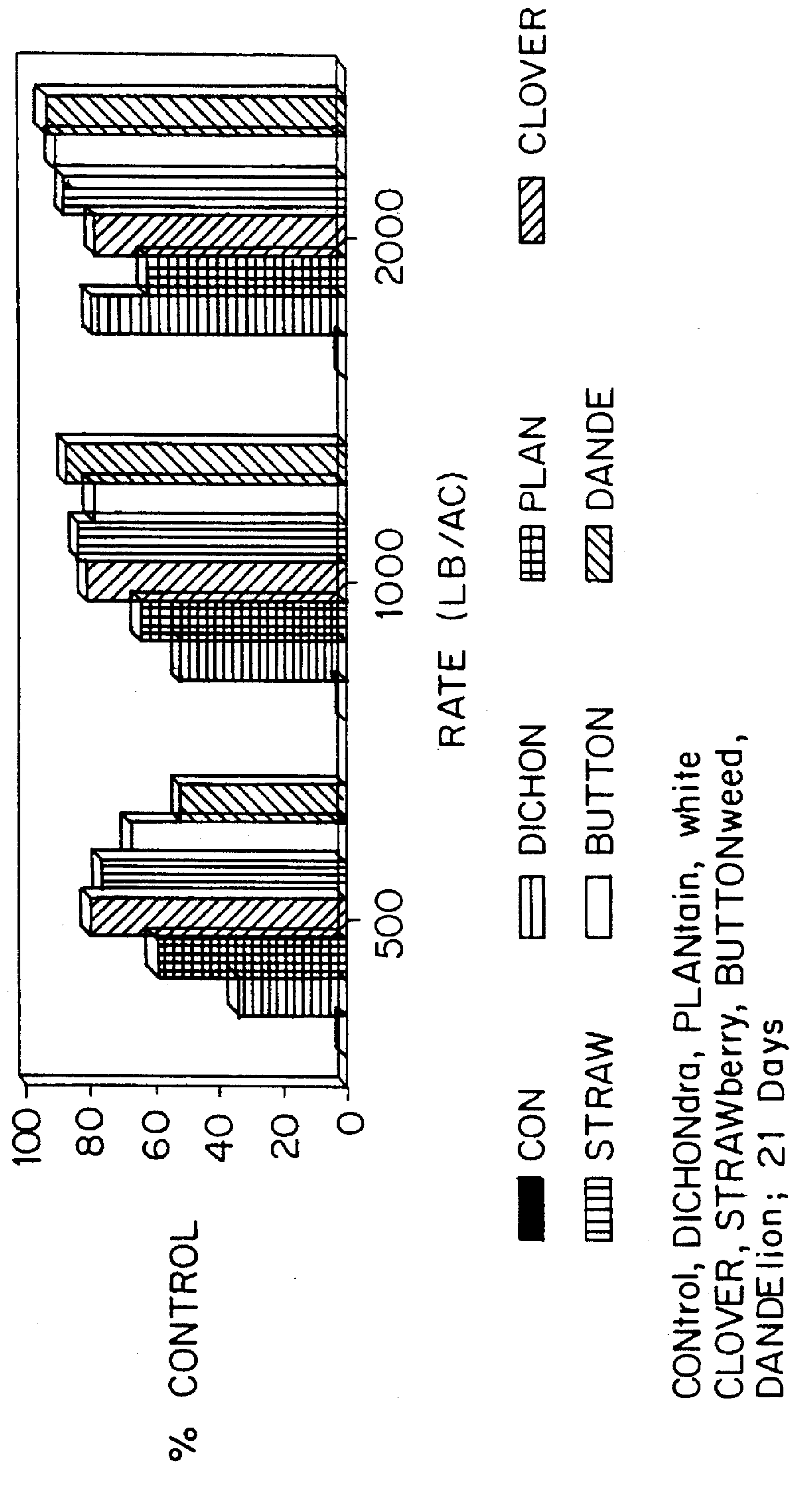
FIG. 4 illustrates the efficacy of wild-type strain *S. sclerotiorum* 84.1B after 21 days.

FIG. 4 illustrates the efficacy of wild-type strain *S. sclerotiorum* 84.1B against several varieties of plants after 21 days. Also, compared were the application rates of 500, 1000, and 2000 pounds of active ingredient per acre. The plant species tested against as shown in this figure are control, dichondra, plantain, white clover, mock strawberry, buttonweed, and dandelion.

Figure 5:
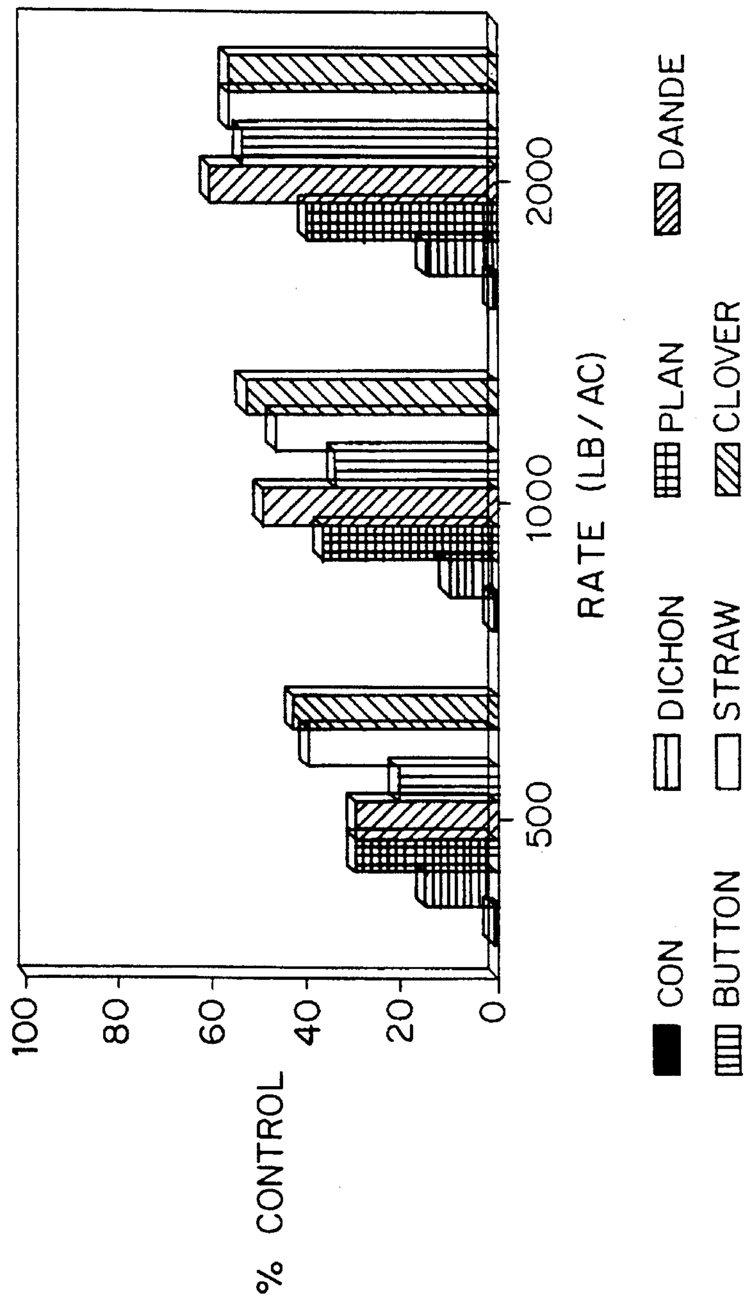
FIG. 5 illustrates the efficacy of a mutant sclerotialess strain *S. sclerotiorum* SL-7 after 10 days.

FIG. 5 illustrates the efficacy of a mutant sclerotialess strain *S. sclerotiorum* SL-7 against several varieties of plants after 10 days. Also, compared were the application rates of 500, 1000, and 2000 pounds of active ingredient per acre. The plant species tested against as shown in this figure are control, dichondra, plantain, white clover, mock strawberry, buttonweed, and dandelion.

Figure 6:
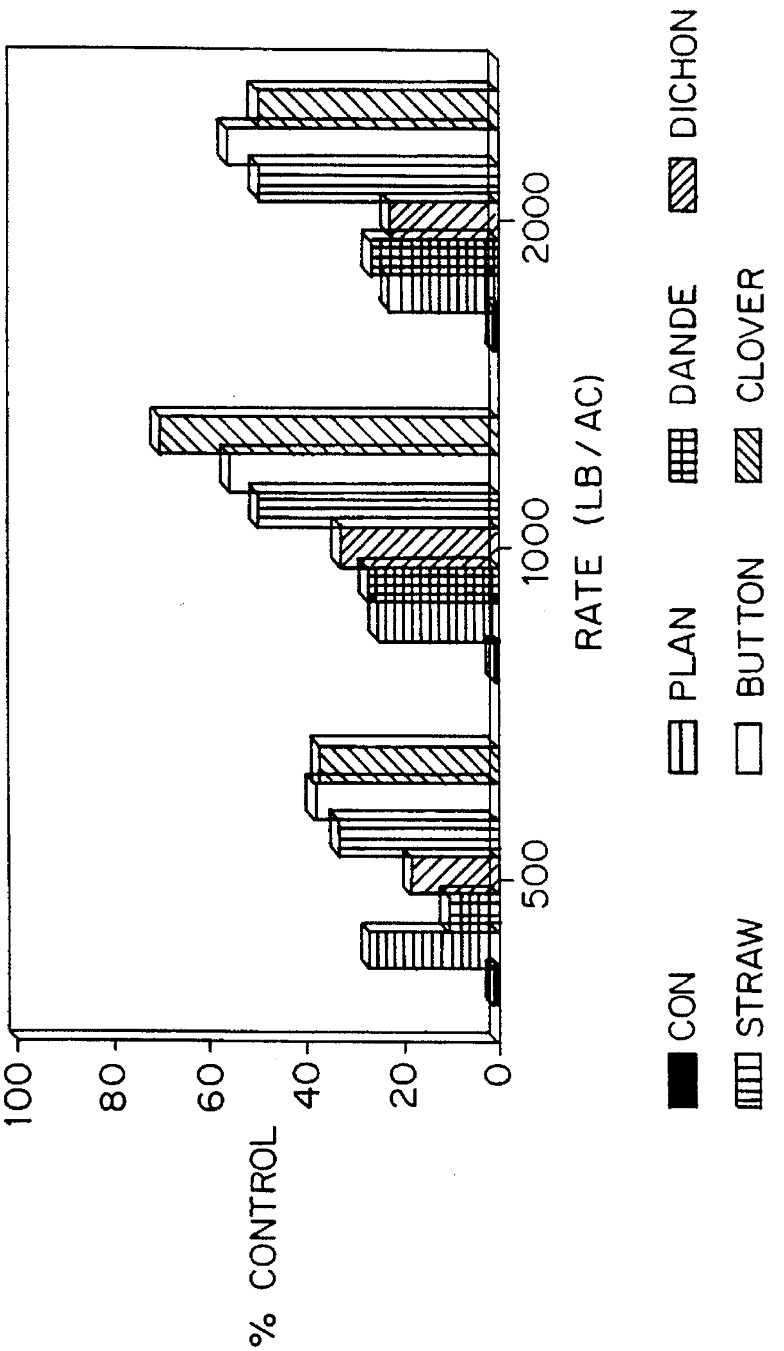
FIG. 6 illustrates the efficacy of a mutant sclerotialess strain *S. sclerotiorum* SL-7 after 21 days.

FIG. 6 illustrates the efficacy of a mutant sclerotialess strain *S. sclerotiorum* SL-7 against several varieties of plants after 21 days. Also, compared were the application rates of 500, 1000, and 2000 pounds of active ingredient per acre. The plant species tested against as shown in this figure are control, dichondra, plantain, white clover, mock strawberry, buttonweed, and dandelion.

Figure 7:
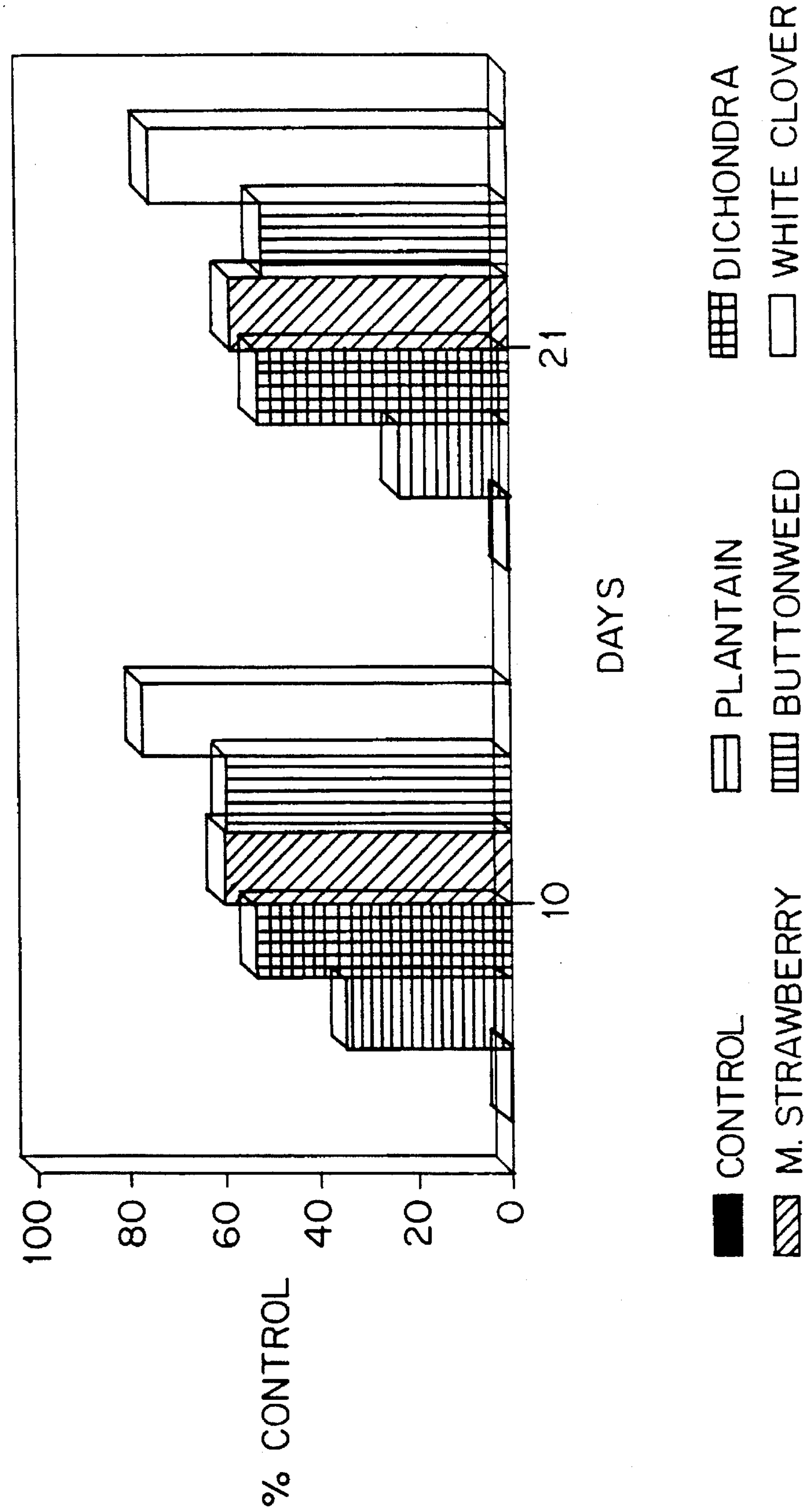
FIG. 7 illustrates the efficacy of a mutant arginine auxotroph strain *S. sclerotiorum* A6-ARG after 10 and 21 days.

FIG. 7 illustrates the efficacy of a mutant arginine auxotroph strain *S. sclerotiorum* A6-ARG against several varieties of plants after 10 and 21 days. Also, compared were the application rates of 500, 1000, and 2000 pounds of active ingredient per acre. The plant species tested against as shown in this figure are control, dichondra, plantain, white clover, mock strawberry, buttonweed, and dandelion.

Figure 8:
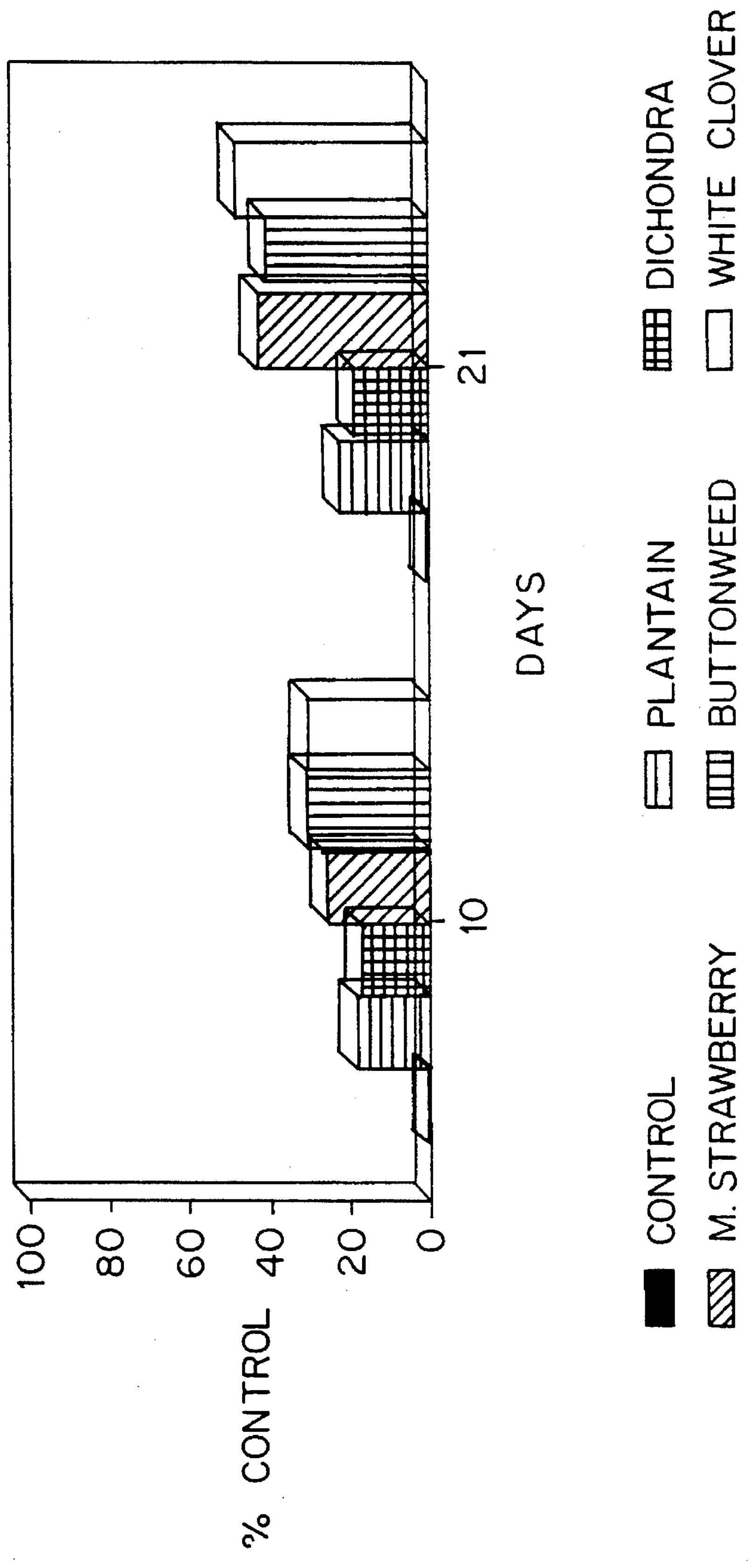
FIG. 8 illustrates the efficacy of a mutant leucine auxotroph strain *S. sclerotiorum* A8-LEU after 10 and 21 days.
Figure 9:
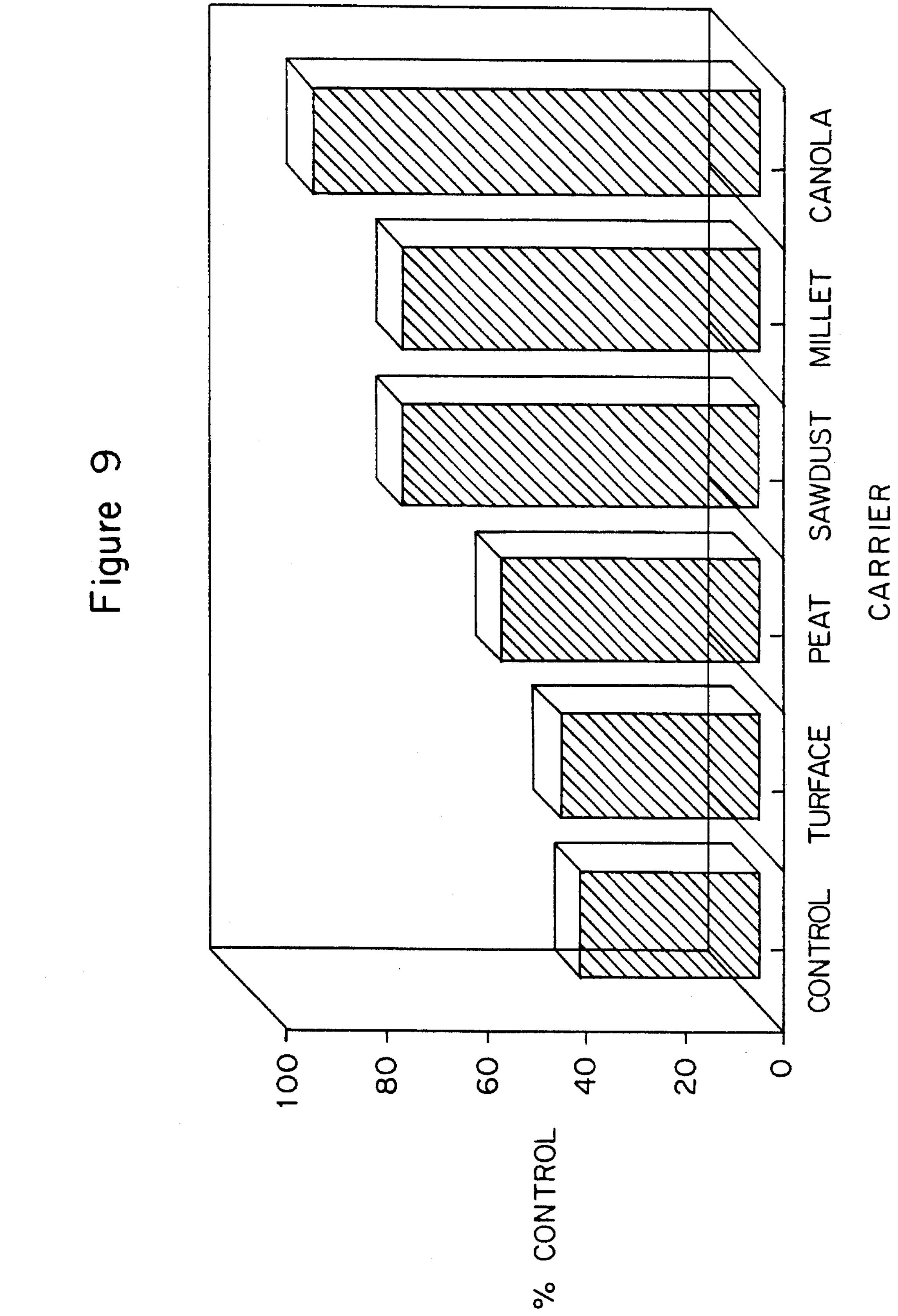
FIG. 9 illustrates the relative efficacies of various formulation having effective amounts of the wild-type *S. sclerotiorum* 84.1B species.

FIG. 8 illustrates the efficacy of a mutant leucine auxotroph strain *S. sclerotiorum* A8-LEU against several varieties of plants after 10 and 21 days. Also, compared were the application rates of 500, 1000, and 2000 pounds of active ingredient per acre. The plant species tested against as shown in this figure are control, dichondra, plantain, white clover, mock strawberry, buttonweed, and dandelion.

FIG. 9 illustrates the relative efficacies of various formulation having effective amounts of the wild-type *S. sclerotiorum* 84.1B species. This virulance contrasts with shelf-life, storage, and viability of various formulations. Having a longer shelf life in one formulation is not necessarily the same as having virulence at the longer shelf life.

The application rates for field application of the active ingredient range from about 10 to about 1000 pounds per acre and preferable from about 5 to about 500 pounds per acre. An effective dosage range for treating a plant area of a plot is about 5 to about 200 $g/m^2$, and preferably about 30 to about 60 $g/m^2$.

Other micorobial pathogens which can be used against particular plants can be isolated from dead plants and then modified using the present method to produce broad range herbicides according to the present invention. For example, herbicides effective against plants such as dandelion plants are obtained from isolates of dead dandelion plants. Examples of isolates are Rhizoctonia, Fusarium, Pseudomonas, Xanthomonas, and other unidentificed bacteria.

The invention now being fully described it will be apparent to one of ordinary skill in the art that many changes and modifications can be made thereto without departing from the spirit or scope of the invention as set forth therein. The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

What is claimed is:

1. A broad spectrum bioherbicide, comprising a biocidal effective amount of a fungal mutant of wild-type fungi selected from the group of subdivisions of fungi consisting of Mastigomycotinia, Zygomycotina, Ascomycotinia, Basidiomycetes, Myxomycota, and Deuteromycotinia; wherein said funqal mutant has a substantially altered phenotype or morphology characteristic selected from the group consisting of pigmentation, mycelial density, mycelial area, mycelial growth rate, sclerotia, and reproductive structures when compared with the wild-type; and said fungal mutant is an auxotrophic mutant having a requirement of at least one nutrient selected from the group consisting of a carbohydrate, a pyridine, a pyrimidine, an amino acid, a fatty acid, and a vitamin; and said fungal mutant survival is dependent upon the presence of the nutrient.

2. The bioherbicide of claim 1, wherein said bioherbicide further comprises an agriculturally acceptable carrier.

3. The bioherbicide of claim 1, wherein said fungal mutant selected from the group consisting of

*Sclerotinia sclerotiorum* Al-Pyr (ATCC Accession No. 20929),

*Sclerotinia sclerotiorum* SL-1 (ATCC Accession No. 20930),

*Sclerotinia sclerotiorum* SL-7 (ATCC Accession No. 74246),

*Sclerotinia sclerotiorum* A6-ARG (ATCC Accession No. 74248),

*Sclerotium rolfsii* SrA6-Pyr (ATCC Accession No. 74247), and

*Sclerotium rolfsii* SrA4-Thi (ATCC Accession No. 74249).

4. The bioherbicide of claim 1, wherein said bioherbicide is incapable of winter over.

5. A broad spectrum bioherbicide according to claim 1, wherein said bioherbicide is obtained by a method comprising:

obtaining viable wild-type fungal cells wherein said wild-type fungal cells are selected from the group of subdivisions of fungal cells consisting of Mastigomycotinia, Zygomycotina, Ascomycotinia, Basidiomycetes, Myxomycota and Deuteromycotinia;

subjecting said fungal cells to mutagenic conditions, wherein said mutagenic conditions are effective to reduce the number of viable fungal cells to less than about 5% of the initial number of fungal cells;

selecting mutant fungal cells which differ from the wild-type fungal cells in that the mutant fungal cells are auxotrophic mutant fungal cells which require cytosine for survival, whereas the wild-type fungal cells do not require a cytosine supplement for survival; and further selecting a mammal-sparing bioherbicide fungal cell auxotrophic mutant with survival dependent upon at least one nutrient selected from the group consisting of a carbohydrate, a pyridine, a pyrimidine, an amino acid, a fatty acid, and a vitamin.

6. The bioherbicide of claim 5, wherein said fungal cells are spores or sclerotia.

7. The bioherbicide of claim 6, wherein said spores are photosensitized by contacting them with a UV sensitizing agent prior to UV treatment.

8. The bioherbicide of claim 7, wherein said spores are placed in a growth medium prior to contacting them with said UV sensitizing agent.

9. The bioherbicide of claim 5, comprising mutant fungal cells incapable of producing spores and capable of infecting and being pathogenic to a broad spectrum of plants while sparing mammals, wherein said mutant fungal cells are unable to winter over whereas the wild-type fungi fungal cells do winter over.

10. The bioherbicide of claim 1, wherein said fungal mutant differs from the wild-type fungi in that said fungal mutant is substantially unable to produce spores or sclerotia, whereas the wild type fungi can produce spores or sclerotia.

11. A broad spectrum bioherbicide comprising (a) a fungal mutant according to claim 1, and (b) at least one nutrient selected from the group consisting of a carbohydrate, a pyridine, a pyrimidine, an amino acid, a fatty acid or a vitamin.

12. The bioherbicide kit of claim 11, wherein said fungal mutant survival is dependent upon the presence of the nutrient.

13. The bioherbicide of claim 11, wherein said nutrient comprises cytosine.

14. A method of obtaining a broad spectrum bioherbicide, comprising obtaining viable wild-type fungal cells wherein said wild-type fungal cells are selected from the group of subdivisions of fungi consisting of Mastigomycotinia, Zygomycotina, Ascomycotinia, Basidiomycetes, Myxomycota and Deuteromycotinia;

subjecting said cells to mutagenic conditions, which conditions are effective to reduce the number of viable fungi from said cells to less than about 5% of the initial number of cells;

selecting fungal mutant cells which differ from the wild-type fungal cells wherein said fungal mutant cells have a substantially altered phenotype or morphology characteristic selected from the group consisting of pigmentation, mycelial density, mycelial area, mycelial growth rate, sclerotia, and reproductive structures when compared with the wild-type; and said fungal mutant is an auxotrophic mutant having a requirement of at least one nutrient selected from the group consisting of a carbohydrate, a pyridine, a pyrimidine, an amino acid, a fatty acid, and a vitamin; and said fungal mutant survival is dependent upon the presence of the nutrient; and further selecting bioherbicide fungal mutant cells wherein the survival of said mutant cells is dependent upon the presence of said at least one nutrient.

15. The method of claim 14, wherein said mutagenic conditions are produced by exposing said cells to either ultraviolet (UV) light or chemical mutagenic agents.

16. The method of claim 15, further comprising the step of photosensitizing said cells by contacting them with a UV sensitizing agent prior to exposure to UV light.

17. The method of claim 16 further comprising placing said cells in a growth medium prior to contacting them with said UV sensitizing agent.

18. The method of claim 14, wherein the fungal mutant cells are morphologically different from the wild-type fungal cells in at least one characteristic selected from the group consisting of an inability to produce spores or an inability to produce *sclerotia* and germtubes from spores, wherein said wild-type fungal cells will produce said spores or said *sclerotia* and germtubes from spores.

19. A method according to claim 14 wherein said fungal cells are selected from the group consisting of spores and *sclerotia*.

20. A method according to claim 14 wherein said fungal cells are spores.

* * * * *